Figure 1:
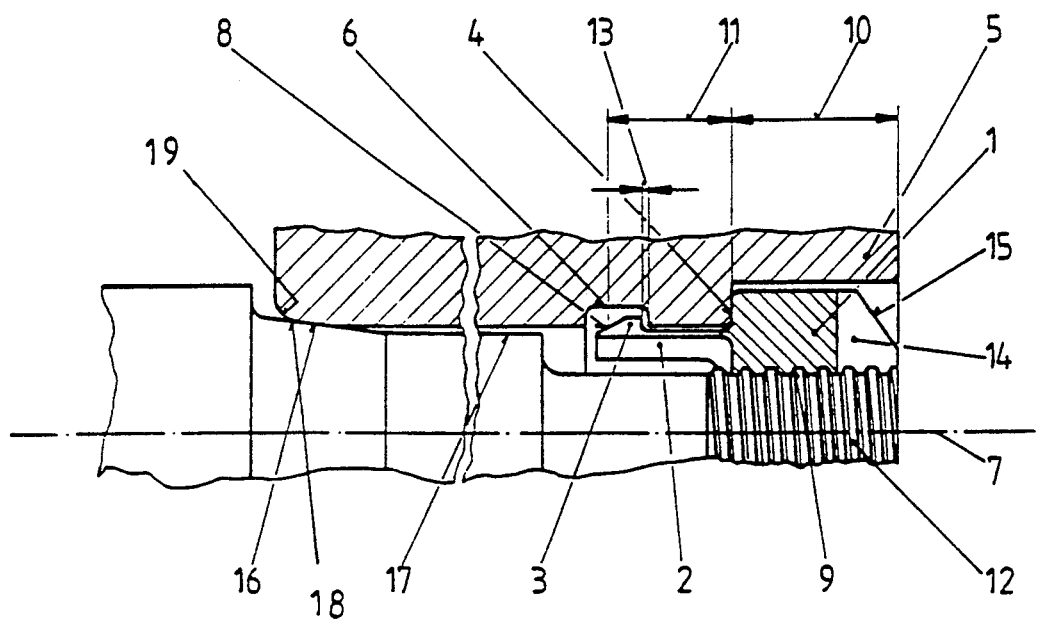

United States Patent [19]
Moser et al.

[11] Patent Number: 5,330,535
[45] Date of Patent: Jul. 19, 1994

[54] SCREW-NUT FOR SCREWING IMPLANTS TOGETHER

[75] Inventors: Walter Moser, Herrenschwanden; Roland Willi, Netterbach, both of Switzerland

[73] Assignees: Sulzer Brothers Limited, Winterthur; Protek AG, Berne, both of Switzerland

[21] Appl. No.: 52,220

[22] Filed: Apr. 22, 1993

Related U.S. Application Data

[63] Continuation of Ser. No. 848,091, Mar. 9, 1992, abandoned.

[30] Foreign Application Priority Data

Mar. 7, 1991 [CH] Switzerland ............... 00692/91-3

[51] Int. Cl.$^5$ ............................................. A61F 2/38
[52] U.S. Cl. ........................................ 623/20; 623/18
[58] Field of Search ................. 623/16, 18, 19, 20

[56] References Cited

U.S. PATENT DOCUMENTS 3,053,357  9/1962  Stanger ................... 403/21
4,822,366  4/1989  Bolesky ................... 623/20
4,936,853  6/1990  Fabian et al. ............ 623/20

FOREIGN PATENT DOCUMENTS 3017953  2/1981  Fed. Rep. of Germany.

Primary Examiner—David Isabella
Attorney, Agent, or Firm—Kenyon & Kenyon

[57] ABSTRACT

A screw-nut for screwing implants together includes a thrust-shoulder which projects radially and presses axially against part of a housing. The screw-nut further includes an internal threaded portion adapted to fit a corresponding screw part, and a plurality of members, each mounted onto the side of the thrust-shoulder facing away from the part of the housing against which the thrust shoulder presses. These members are adapted to receive a tool for tightening the screw-nut. A plurality of leaf springs is included for engaging the housing part. The leaf springs, the ends of which form latching-in dogs, project, in the axial direction, from the screw-nut. The leaf springs are constructed such that, when the thrust-shoulder makes contact with the housing part, each latching-in dog snaps into a recess in the housing part in order to prevent loosening of the screw-nut from the housing part.

6 Claims, 1 Drawing Sheet

SCREW-NUT FOR SCREWING IMPLANTS TOGETHER

This is a continuation of Ser. No. 07/848,091, filed Mar. 9, 1992, now abandoned.

The invention deals with a screw-nut for screwing implants together, having a thrust-shoulder which projects radially and presses axially against part of a housing, and having an internal thread which fits a screw part and members moulded onto the side facing away from the housing part in order to insert a tool for tightening the screw-nut.

In contrast to the rigid connections of machine construction it would, in the case of certain connections between components of implants, be highly advantageous if micro-movements between the components were possible in order to take into account the elasticity of the bone tissue growing in and the intermediate alterations in the bone tissue. Thus the EP-OS 0 333 642 A1 shows an anchoring plate for the bearing areas of a tibia, which is connected to anchoring studs through a screw connection which my be loosened from outside.

One disadvantage of the connection lies in the fact that—because of the securing of the screw connection—it is made rigid and reproduces movements of the tibia plate with respect to the bone tissue in an unrestricted manner at the anchoring studs.

Here the invention creates a remedy. It solves the problem of securing, in the tibia plate, an anchoring stud which is anchored in the bone tissue, in such a way that, through a screw connection, that micro swinging movements can take place between the anchoring studs and the tibia plate.

In accordance with the invention, the problem is solved by leaf springs, projecting in the axial direction, being moulded onto the screw-nut and ending in latching-in dogs. In addition, the fact that, with the thrust-shoulder making contact with the housing part, the latching-in dogs snap into a recess in the housing part in order to prevent loosening of the screw-nut from the housing part.

The advantage of the invention consists in the fact that, for a limited range with the occurrence of a bending moment in the clamping of the anchoring stud, a swinging movement occurs which grows with the bending moment without the members for screwing together the tibia plate being able to loosen in the long term.

Figure 2:
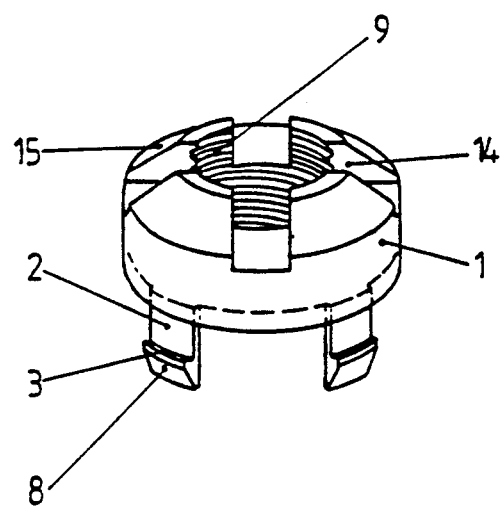

The invention is described below with the aid of an embodiment. There is shown diagrammatically in:

FIG. 1 - a section through the anchoring of an anchoring stud in a tibia plate by a screw connection; and FIG. 2 - the perspective of a screw-nut shown in FIG. 1.

The Figures show a screw-nut for screwing implants together, having a thrust-shoulder which projects radially and presses axially against part of a housing, and having an internal thread which fits a screw part and members moulded onto the side facing away from the housing part in order to insert a tool for tightening the screw-nut. In accordance with the invention, leaf springs which project in the axial direction are moulded onto the screw-nut and end in latching-in dogs. Upon pressing the screw-nut into the housing part, with the thrust-shoulder making contact, the latching-in dogs snap in to a recess in the housing part in order to prevent loosening of the screw-nut from the housing part.

As shown in FIG. 1, an anchoring stud is inserted in a cylindrical hole drilled in a part 5 of a housing made as a tibia plate and is secured axially by a screw-nut 1. The stud is seated by a short taper part 16 along a line contact 18 area with a rounded corner 19 at the entrance to the drilled hole whilst the cylindrical part 17 adjoining it exhibits play with respect to the drilled hole in order to be able to perform small swinging movements referred to the clamping at the taper part 16. The anchoring stud ends at the outside of the tibia plate as a threaded bolt with a screwed part 12 upon which the screw-nut 1 rides by the internal thread 9.

In FIG. 2 a screw-nut 1 may be seen, from which four leaf springs 2 project in the axial direction to end in latching-in dogs 3, these latching-in dogs having, in the direction of insertion, oblique or rounded run-up faces 8 and, in the direction of extraction, steep latching-in faces.

Upon entering the screw-nut 1 into the part 5 of the housing, the leaf springs are prestressed by the running-up faces 8 running up radially inward until the latching-in dogs—at the latest as the thrust-shoulder 4 makes contact—snap in to a recess 6 in the part 5 of the housing. With the thrust shoulder 4 resting against the housing part 5 a clearance 13 in the direction of the axis 7 of the screw results between the latching-in dogs 3 and a counterface on the housing part 5, which is so dimensioned that the latched-in screw-nut 1 is supported to be able to turn in the housing part 5. On the side facing away from the housing part the screw-nut 1 has shaped members 14 in the form of slots in which a tool can engage in order to tighten the nut. Even if upon first screwing the screw-nut 1 onto the anchoring stud it has been pulled tight it is not assumed that the axial prestress is maintained. Micro movements and settling in the taper part loosen the connection between the screw part 12 and internal thread 9, so that the planned swinging movements of the anchoring stud with respect to the housing part 5 can take place without the screw-nut 1 loosening inadmissibly from the housing part 5, thanks to the latching-in.

The screw-nut 1 may be premounted in the housing part 5 by being pressed axially into the housing part until the thrust shoulder 4 seats. After the insertion of the anchoring stud in the tibia part the housing part 5 made as the tibia plate is run in over the screw part 12 until the internal thread 9 seats and by turning the screw-nut 1 is brought along until in its final position.

Another possibility consists in inserting the anchoring stud almost home, mounting the tibia plate over the screw part 12 until the taper part 16 engages and inserting both parts together as far as the final position. Then the screw-nut 1 is mounted and turned in along the screw part 12 until the thrust-shoulder 4 strikes against the housing part and latching-in by the latching-in dogs 3 takes place. In FIG. 1 the screw part 12 terminates at the outer face of the tibia plate. The counterface for the thrust-shoulder 4 is set back inside by a length 10. The axial distance 11, between the internal thread 9 and the point of contact on the run-up faces 8 which first runs up against the housing part 5, is clearly less than the length 10 so that a movement pressing inward is effected through the internal thread 9 engaging and a torque being applied to the screw-nut 1. The turning in of the screw-nut is effected by an auxiliary tool which may be centered on a bevel 15 on the screw-nut and engages in the slots 14 in order to transmit the necessary torque.

What is claimed is:

1. An implant comprising:

a tibia plate which, when in an operative position, settles on a resected tibia bone to form a platform for an artificial knee, the tibia plate including a stem receiving recess;

a stem projecting into the stem receiving recess of the tibia plate, wherein the stem is connected to the tibia plate for enhancing side-hold and for preventing withdrawal of the tibia plate, wherein:

a portion of the stem which, when in the operative position, contacts a lower plane of the tibia plate, consists of a cone with a small half angle which fits into a cylindrical bore in the tibia plate, the cylindrical bore including a rounded corner to produce line contact between the stem and the lower plane of the tibia plate;

and wherein a clearance exists between the cylindrical bore and the projecting stem in the direction of an upper plane of the tibia plate, the clearance being sized to allow the tibia plate to be substantially inclined out of a position perpendicular to the stem axis towards the stem axis;

the implant further including a screw-nut inserted from the top of the plate to press against a shoulder of the plate in an upper plane of the tibia plate and fixing the stem in the operative position while allowing the inclination of the tibia plate toward or away from the stem axis.

2. An implant according to claim 1, wherein a portion of the stem which, when in the operative position, is located between the upper and lower planes of the tibia plate has a reduced bending stiffness relative to the portion of the stem which is located below the lower plane of the tibia plate to allow the tibia plate to follow an elastic deformation of the tibia bone by further inclination with reference to the lower plane.

3. An implant according to claim 1, wherein the screw-nut includes a thrust shoulder and a plurality of leaf springs for engaging the shoulder of the tibia plate, each leaf spring projecting in the axial direction away from the screw-nut wherein the end of each leaf spring forms a latching-in dog which, when the thrust shoulder of the screw-nut contacts the shoulder of the tibia plate, snaps into a recess in the cylindrical bore of the tibia plate to prevent loosening of the screw-nut from the tibia plate.

4. An implant according to claim 3, wherein each latching-in dog includes a run-up face which, upon the leaf spring being run into the cylindrical bore of the tibia plate, is prestressed in order to execute a latching-in motion, upon the thrust-shoulder making contact with the housing part.

5. An implant according to claim 1, wherein the stem includes a screw portion and the screw-nut includes a corresponding internal threaded portion, wherein the length, in the axial direction, of the internal threaded portion is greater than the distance from the point of contact between the tibia plate and the leaf springs so that deformation of the leaf springs may be performed by a screwing motion engaging the internal threaded portion with the corresponding screw part so that the screw part does not project axially beyond the screw-nut in the final mounted position.

6. An implant according to claim 3, wherein a clearance in the axial direction exists between each of the latching-in dogs and a counterface on the tibia plate such that the screw-nut may be turned with respect to the tibia plate part while latched into the tibia plate.

* * * * *